(12) United States Patent
Alford et al.

(10) Patent No.: US 10,197,538 B2
(45) Date of Patent: Feb. 5, 2019

(54) SYSTEMS AND APPARATUS FOR INSPECTION OF ELECTRIC GENERATOR ROTOR SLOT WEDGES IN-SITU AND METHODS OF USING THE SAME

(71) Applicant: Siemens Energy, Inc., Orlando, FL (US)

(72) Inventors: James Alford, North Huntingdon, PA (US); Charles C. Moore, Hibbs, PA (US); El Mahjoub RasselKorde, Monroeville, PA (US); James A. Bauer, Gibsonia, PA (US); Joseph T. Beuten, Adamsburg, PA (US)

(73) Assignee: SIEMENS ENERGY, INC., Orlando, FL (US)

( * ) Notice: Subject to any disclaimer, the term of this patent is extended or adjusted under 35 U.S.C. 154(b) by 183 days.

(21) Appl. No.: 15/013,416

(22) Filed: Feb. 2, 2016

(65) Prior Publication Data
US 2017/0219533 A1    Aug. 3, 2017

(51) Int. Cl.
| | |
|---|---|
| *G01N 29/26* | (2006.01) |
| *G01N 29/22* | (2006.01) |
| *G01N 29/04* | (2006.01) |
| *G01N 27/90* | (2006.01) |

(Continued)

(52) U.S. Cl.
CPC ............. *G01N 29/26* (2013.01); *G01N 27/90* (2013.01); *G01N 29/04* (2013.01); *G01N 29/225* (2013.01); *G01N 29/262* (2013.01); *G01N 29/265* (2013.01); *G01N 29/28* (2013.01); *G01N 2291/106* (2013.01); *G01N 2291/2693* (2013.01)

(58) Field of Classification Search
CPC ........ G01N 29/26; G01N 27/90; G01N 29/04; G01N 29/225; G01N 29/262; G01N 29/265; G01N 29/28; G01N 2291/106; G01N 2291/2693
USPC .......................................................... 73/632
See application file for complete search history.

(56) References Cited

U.S. PATENT DOCUMENTS

| | | | |
|---|---|---|---|
| 5,650,579 A * | 7/1997 | Hatley ................. | B62D 55/065 348/E7.086 |
| 6,298,727 B1 * | 10/2001 | Fleming ................. | G01N 29/22 73/642 |
| 6,672,413 B2 | 1/2004 | Moore et al. | |

(Continued)

FOREIGN PATENT DOCUMENTS

| | | |
|---|---|---|
| JP | H03089828 A | 4/1991 |
| JP | H042869955 A | 10/1992 |

(Continued)

*Primary Examiner* — Natalie Huls
*Assistant Examiner* — Monica S Young (57) ABSTRACT

System, methods, and devices for inspecting generator rotor slot wedges in-situ are provided. The system includes a controller operably connected to a remote-control carriage for transmitting control signals and receiving data. The carriage includes a drive module for moving the carriage into an inspection area, e.g., through an air gap between the rotor and stator, and an inspection module operable to inspect a rotor wedge surface. The inspection module includes a jack assembly and a transducer assembly. The jack assembly is operably connected to the transducer assembly, and configured to elevate the transducer assembly to the rotor wedge surface for inspection.

19 Claims, 6 Drawing Sheets

(51) Int. Cl.
    *G01N 29/265*     (2006.01)
    *G01N 29/28*     (2006.01)

(56) References Cited

U.S. PATENT DOCUMENTS

| | | | |
|---|---|---|---|
| 6,889,783 B1 | 5/2005 | Moore et al. | |
| 7,201,055 B1* | 4/2007 | Bagley | G01R 31/34 |
| | | | 376/249 |
| 7,743,675 B2 | 6/2010 | Moore | |
| 7,866,421 B2 | 1/2011 | Moore et al. | |
| 2002/0104693 A1* | 8/2002 | Moore | B62D 57/024 |
| | | | 180/9.1 |
| 2004/0020002 A1* | 2/2004 | Moore | B62D 57/024 |
| | | | 15/340.1 |
| 2007/0089544 A1 | 4/2007 | Bagley et al. | |
| 2008/0087112 A1* | 4/2008 | Bagley | G01N 29/265 |
| | | | 73/865.8 |
| 2008/0087113 A1* | 4/2008 | Bagley | G01H 9/008 |
| | | | 73/865.8 |
| 2011/0184661 A1* | 7/2011 | Reed | G01B 11/14 |
| | | | 702/34 |

FOREIGN PATENT DOCUMENTS

| | | |
|---|---|---|
| JP | 2001116728 A | 4/2001 |
| JP | 2002209363 A | 7/2002 |

\* cited by examiner

SYSTEMS AND APPARATUS FOR INSPECTION OF ELECTRIC GENERATOR ROTOR SLOT WEDGES IN-SITU AND METHODS OF USING THE SAME

TECHNICAL FIELD

This present disclosure relates generally to electrical generators, and more particularly, to its rotor slot wedges and systems and methods for inspecting the same.

BACKGROUND

Generator rotor slot wedges are generally installed between rotor teeth to hold the copper windings in place. During the course of operation one or more wedges may develop flaws, e.g., surface cracks, which may lead to a failure of the generator. Inspection of the rotor wedge surface is therefore recommended for maintaining generator operability. Cracks initiating from the side of the rotor wedges are generally not accessible for a surface inspection, or more particularly a volumetric inspection, without removing the rotor. One of the difficulties in inspecting the rotor wedges without removing the rotor is that there is a small clearance, e.g., as little as between 0.6 inch (1.52 cm) and 1.5 inches (3.81 cm), between the stator bore and the rotor retaining ring through which an apparatus may be inserted to inspect the wedges distributed along the length of the stator. Because of this limited clearance, inspection is typically performed by removing the generator rotor from the stator frame to provide access to the rotor wedges, while the wedges remain installed in the rotor. This method of inspection, i.e., by removing the rotor, requires a significant amount of time during the outage, and increases the risk of damage to the rotor and stator.

Therefore, there remains a need for a more efficient means of inspecting the rotor wedges without having to remove the generator rotor, and risking damage to the rotor and stator.

SUMMARY

In one exemplary embodiment, a generator inspection vehicle is provided. The inspection vehicle may be sized and configured to fit within an air gap between a stator and a rotor of the generator, the air gap may be, e.g., 1.6 inches. The vehicle includes a frame, a drive module selectively attached to the frame for maneuvering the vehicle on an interior surface of the generator, and an inspection module selectively attached to the frame and operable to extend and retract in response to control signals from a remote device, and to inspect a rotor wedge surface of the generator in-situ in the extended position.

In another exemplary embodiment, a system for inspecting generator rotor slot wedges in-situ is provided. The system includes a controller operatively connected to an inspection vehicle. The controller is configured to maneuver the vehicle within a generator, via control signals, and to receive image data from the vehicle during the in-situ inspection. The vehicle is sized and configured to fit through an air gap between a stator and a rotor of the generator and into an inspection area or passage. The vehicle is operably configured to elevate a transducer assembly carried by the vehicle to a rotor wedge surface for inspection. And the transducer assembly is configured to inspect the wedge surface in response to the control signals.

In yet a further exemplary embodiment, a method for inspecting generator rotor slot wedges in-situ is provided. The method includes the step of: maneuvering an inspection vehicle, via a remote controller, through an air gap of a generator and into alignment with a rotor slot wedge for inspection. The method further includes the step of: elevating at least a portion of the inspection vehicle to a surface of the rotor slot wedge such that the portion of the inspection vehicle is proximate or adjacent to the surface. The next step in the method is to inspect the surface, via a transducer of the inspection vehicle, by capturing image data corresponding to the surface and transmitting the image data to the remote controller.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which.

DETAILED DESCRIPTION

The components and materials described hereinafter as making up the various embodiments are intended to be illustrative and not restrictive. Many suitable components and materials that would perform the same or a similar function as the materials described herein are intended to be embraced within the scope of embodiments of the present invention.

In general, the computing systems and devices described herein may be assembled by a number of computing components and circuitry such as, for example, one or more processors (e.g., Intel®, AMD®, Samsung®) in communication with memory or other storage medium. The memory may be Random Access Memory (RAM), flashable or non-flashable Read Only Memory (ROM), hard disk drives, flash drives, or any other types of memory known to persons of ordinary skill in the art and having storing capabilities. The computing systems and devices may also utilize cloud computing technologies, via the internet, to facilitate several functions, e.g., storage capabilities, executing program instructions, etc., as described in further detail below. The computing systems and devices may further include one or more communication components such as, for example, one or more network interface cards (MC) or circuitry having analogous functionality, one or more one way or multi-directional ports (e.g., bi-directional auxiliary port, universal serial bus (USB) port, etc.), in addition to other hardware and software necessary to implement wired communication with other devices. The communication components may further include wireless transmitters, a receiver (or an integrated transceiver) that may be coupled or connected to broadcasting hardware of the sorts to implement wireless communication within the system, for example, an infrared transceiver, Bluetooth transceiver, or any other wireless communication know to persons of ordinary skill in the art and useful for facilitating the transfer of information. Additionally, a power supply/pack (e.g., hard wired, battery, etc.) may be included in any of the computing devices described herein. These power supplies may also include some form of redundancy or a backup power means known to persons of ordinary skill and for maintaining the functionality of the computing devices and/or components described herein.

Figure 1:
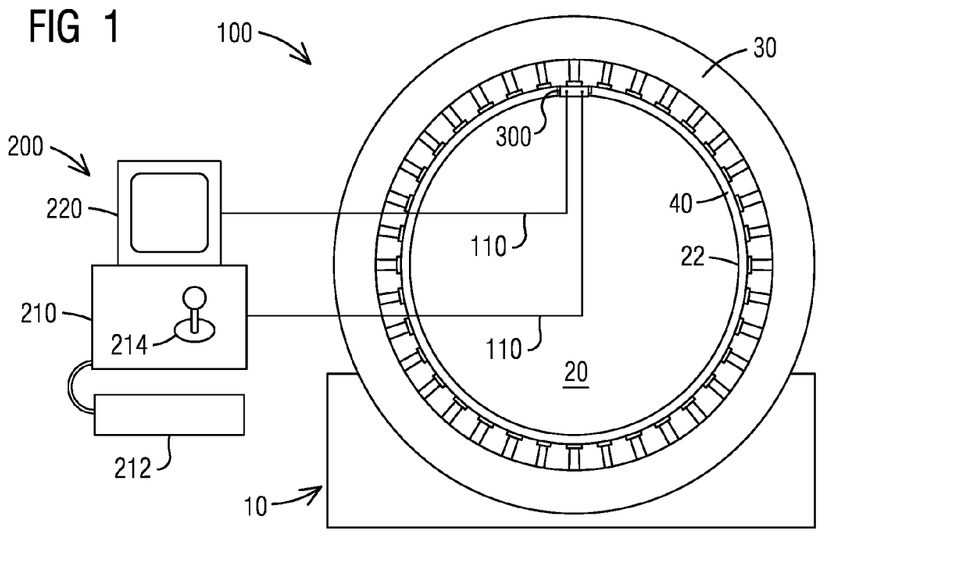
FIG. 1 is a schematic view of a generator with an inspection system, in accordance with the disclosure provided herein.
Figure 2:
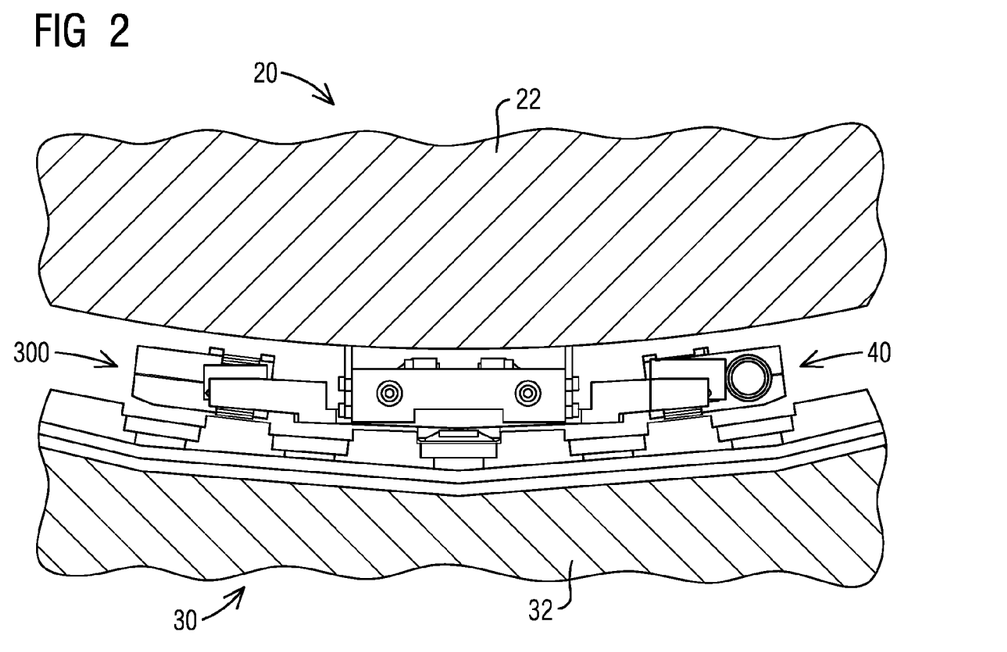
FIG. 2 is a sectional front view of a portion of a generator rotor and stator showing an exemplary embodiment of a remote controlled inspection vehicle seated in an air gap, in accordance with the disclosure provided herein.
Figure 3:
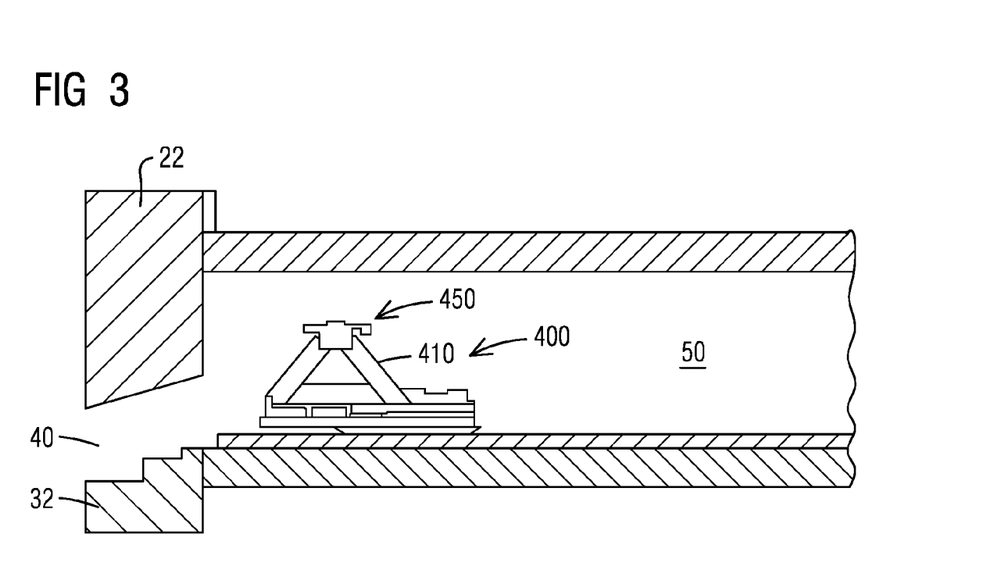
FIG. 3 is a side view of FIG. 2 with the remote controlled inspection vehicle past a restriction point and onto a stator core, in accordance with the disclosure provided herein.

Referring now to the drawings wherein the showings are for purposes of illustrating embodiments of the subject matter herein only and not for limiting the same, FIG. 1 illustrates a dynamoelectric machine 10, e.g., a generator, with system 100 for inspecting generator rotor slot wedges in-situ (also referred to herein as inspection system). The generator 10 may include a rotor 20 mounted for rotation within a stator 30. Referring now to FIGS. 2 and 3, a narrow air gap 40 may be formed between a retaining ring 22 of the rotor 20 and step irons 32 of the stator 30.

The system 100 may include one or more controllers 200 operatively connected to a carriage 300 (also referred to herein as an inspection vehicle) for controlling one or more operations of the carriage 300 and/or its assemblies.

The controller 200 may be connected to the carriage 300 via a wired connection, e.g., via one or more electrical cables 110, or via a wireless connection, e.g., via one or more wireless transceivers. The electrical cables 110 may carry one or more electrical signals from the controller 200 to the carriage 300 for maneuvering and positioning the carriage 300 throughout the generator 10, and may also be used for carrying image signals from the carriage 300 to the controller 200.

The controller 200 may include any combination of the components and/or circuitry described above for remotely controlling the carriage 300, e.g., network interface devices, and for facilitating the transfer of information within the system 100, e.g., between the carriage 300 and the controller 200. The controller 200 may further include a user interface. The user interface may be any general interface for receiving operator input and generating a displayable output on a display 220 operatively connected to the controller 200. As shown in FIG. 1, the user interface may include a keypad 212 and control stick 214 through which the operator may interface with and control the inspection system.

Figure 4:
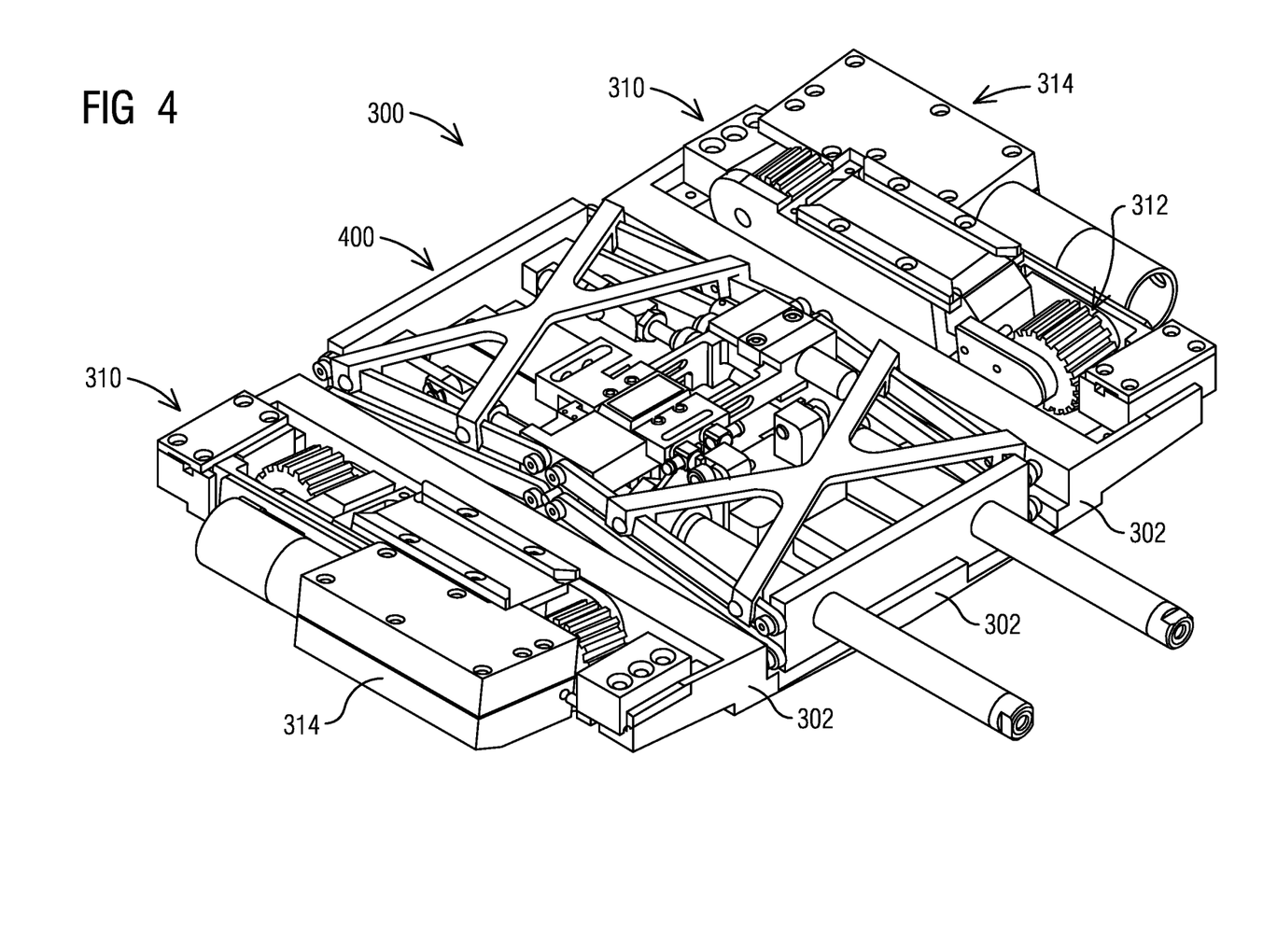
FIG. 4 is a perspective view of another exemplary embodiment of the remote controlled inspection vehicle, in accordance with the disclosure provided herein.

With continued reference to the figures and now to FIG. 4, a perspective view of an exemplary embodiment of the remote controlled carriage 300 is shown. The carriage 300 may be a motorized steerable carriage having a low-profile such the carriage 300 may be inserted in the narrow air gap 40 of the generator 10. Additionally, the carriage may further include a bow-like (arcuate) profile such that the carriage 300 conforms to the concentric circular elements of the generator 10. As illustrated in FIG. 3, the low-profile allow for the carriage 300 to move through the air gap 40 and into an inspection passage 50 where a portion of the carriage, as described in further detail below, may be elevated towards the wedge surface for inspection.

In the embodiment of FIG. 4, the carriage 300 may include one or more drive modules 310 selectively attached to a chassis or frame 302, and disposed on opposite sides of an inspection module 400 also selectively attached to at least a portion of the frame 302.

The frame 302 may be made of a non-electrically conductive, non-magnetically permeable material such a fiberglass. The frame 302 may further include a tail section 304 (FIG. 8) for containing one or more wires, e.g., the electrical cables 110, for supplying electrical power and control signals to the carriage, and for transmitting information detected during the inspection to the controller 200 or other device within the system 100. In one embodiment, the tail section 304 may be as wide as the frame 302, such that it may accommodate the one or more wires and/or hoses (e.g., associated pneumatic hoses). The tail section 304 may also be integrally formed with the frame 302, or selectively attached to the frame 302 as a separate structure and via one or more hinges, e.g., a pivotable hinge, which may allow for the tail section 304 to be flexibly movable, e.g., in an upward or downward direction.

Figure 5:
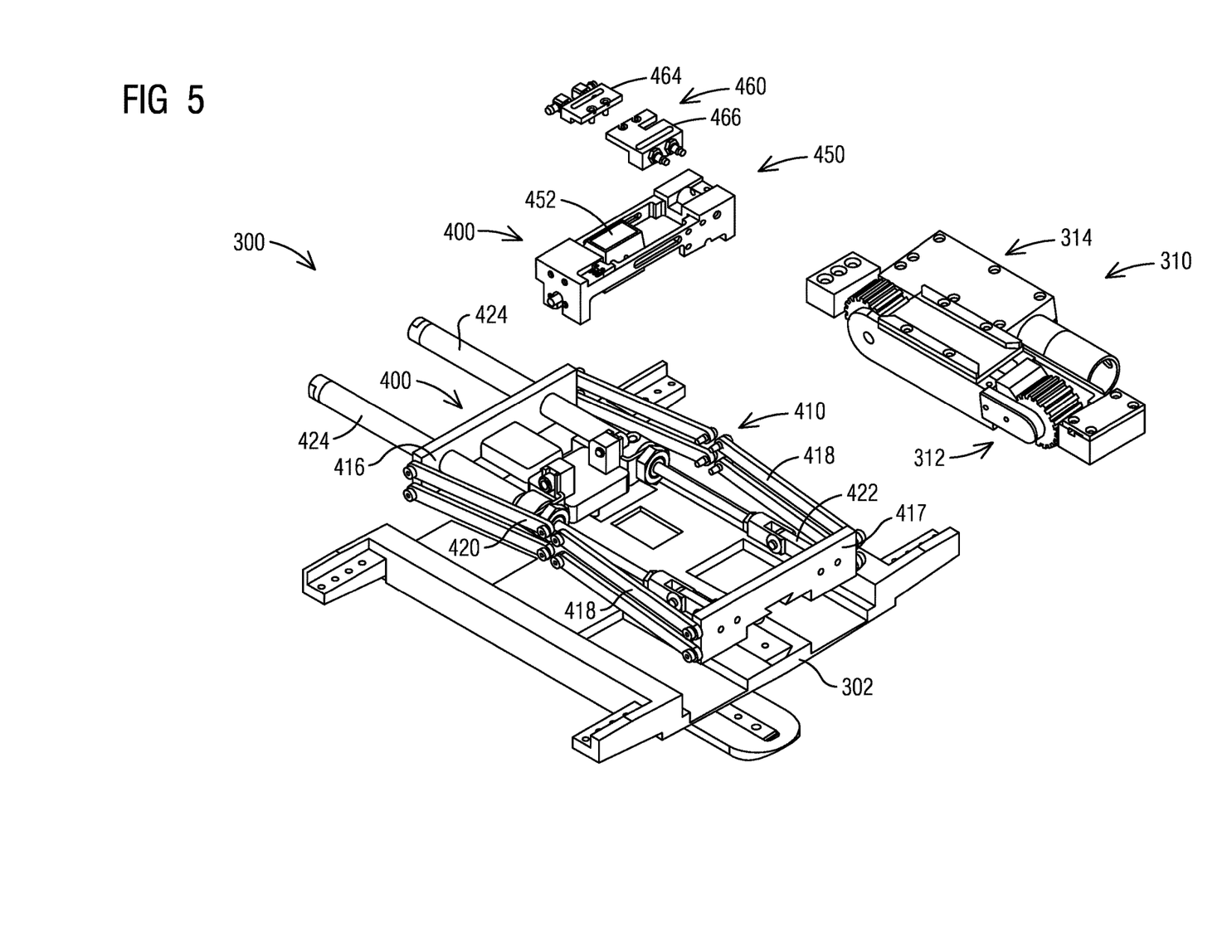
FIG. 5 is an partially exploded perspective view of the remote controlled inspection vehicle, in accordance with the disclosure provided herein.

With continue reference to FIG. 4, and now FIG. 5, the drive module 310 may include a drive train 312 that utilizes magnetic adhesion to traverse an interior ferromagnetic surface of the dynamoelectric machine 10. In one embodiment, the drive module 310 may be attached to the frame 302 via one or more hinge assemblies, which may further allow for the carriage 300 to obtain a bow-like profile. A motor 314 may be operatively connected to the drive module 310 and responsive to one or more signals from the controller 200 to provide a motor force to the drive train 312 for maneuvering the carriage 300 throughout the generator 10. In one embodiment, to assist with positioning the carriage 300 within the generator 10, an encoder (not shown) also driven by the motor may provide signals representing the movement of the carriage to the controller 200 for determining the position of the carriage 300. In yet a further embodiment, a video camera (not shown) or other visual aid may be selectively attached to the carriage 300 to assist with maneuvering the carriage within the generator 10, and to assist with operating the inspection module 400, as will be described further below. In another embodiment, the camera may include lights to provide additionally lighting in a less than desirable light setting. It should also be appreciated that the carriage 300 may include lights selectively attached to the frame 302 or other assembly of the carriage 300, and that the operability of the lights (turning off or on) may be under the control of the controller 200. As described to this point, the drive module 310 drive components, e.g., the motor 314, drive train 312, may be similar to that described in U.S. Pat. No. 6,889,783, issued May 10, 2005 to the assignee of this invention.

With continue reference to FIG. 5, the inspection module 400 is carried by the carriage 300 into the generator 10 and is operatively connected to the controller 200 for receiving one or more command signals for maneuvering throughout an inspection passage in the generator 10, and for inspecting the wedge surface 25. In the embodiment of FIG. 5, the inspection module 400 may include a jack assembly 410 operably configured to extend and retract in response to signals from the controller 200, and a transducer assembly 450 operably configured for a wedge surface 25 inspection, or more particularly, a volumetric inspection. The design of the inspection module 400 allows for the carriage 300 to maintain its low profile, e.g., when the jack assembly is in the retracted position.

Figure 6:
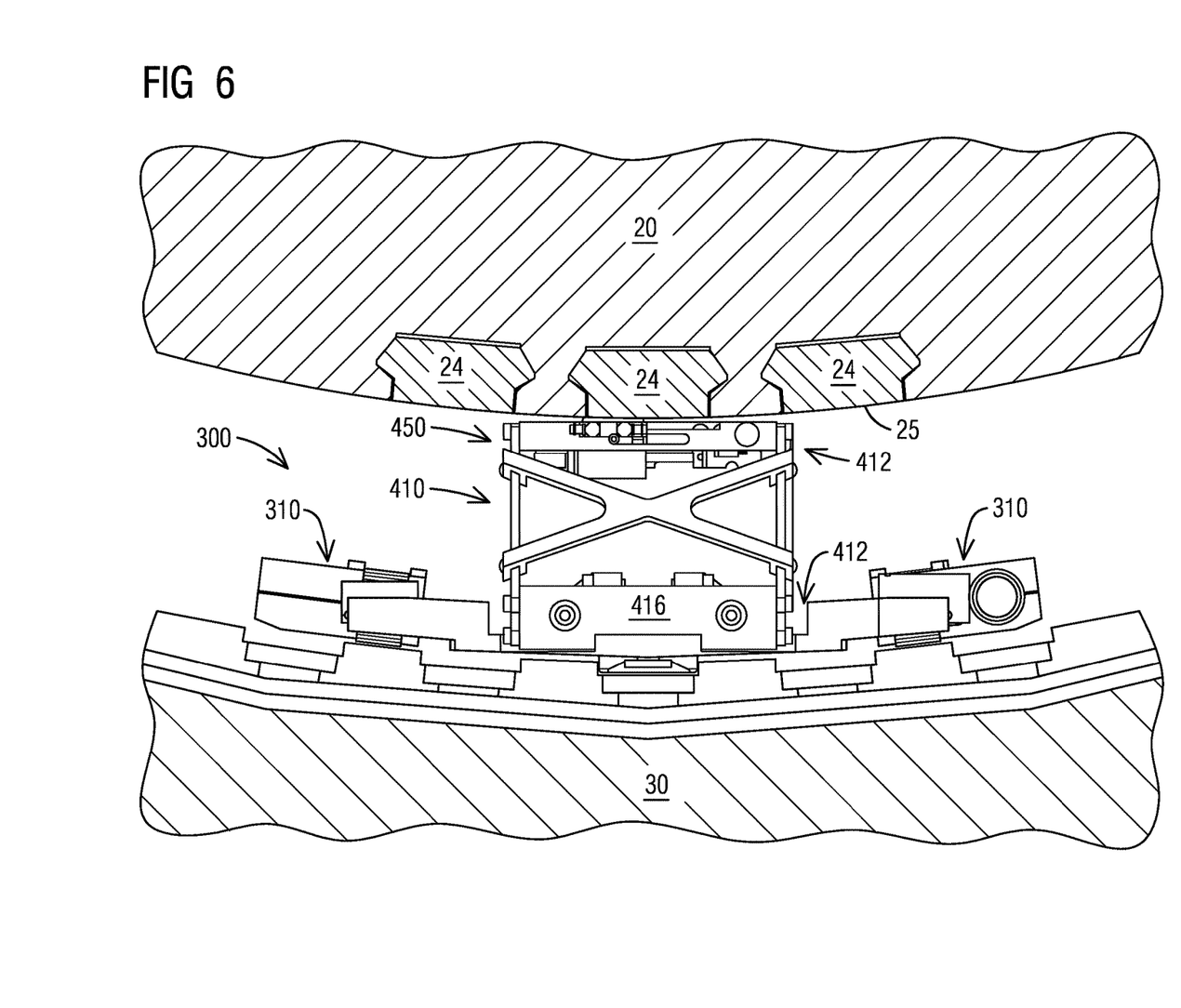
FIG. 6 is a sectional front view of the remote controlled inspection vehicle in an elevated position, in accordance with the disclosure provided herein.

As further illustrated in FIG. 6, the jack assembly includes at least a lower portion 412 adapted for selectively attaching the inspection module 400, or more particularly, the jack assembly 410 to the frame 302, and an upper portion 414 adapted for selectively attaching the transducer assembly 450. In one embodiment, the jack assembly 410 may be a hydraulic jack, scissor jack, screw jack, lever jack, or any other jack operable to provide a means for elevating the transducer assembly 450 to the wedge surface 25 for inspection. It should further be appreciated that any of above embodiments for the jack assembly 410 may be activated hydraulically, pneumatically, electrically, or manually.

In the embodiment of FIG. 5, the jack assembly may include a pair of opposed plates 416, 417 selectively to one or more jack arms 418 and a pneumatic system 420 for elevating the transducer assembly 450, i.e., for expanding and retracting the jack assembly 410. The pneumatic system 420 may be selectively attached to the opposed plates 416, 417 via one or more fasteners secured to, e.g., a piston arm 422 of the pneumatic system, or via one or more apertures or holes in at least one of the opposed plates (FIG. 5, 416), which may be adapted for at least partially receiving one or more pneumatic cylinders 424 of the pneumatic system 420 therebetween. In operation, the pneumatic system 420 may be in operable communication with the controller 200 for receiving command signals to expand or retract the jack assembly 410, e.g., during inspection.

With continued references to figures, the transducer assembly 450 may be selectively attached or placed at the upper portion 414 of the jack assembly, and may include a wedge surface and volumetric inspection means 452. As used herein a transducer is a device that produces sound waves, e.g., ultrasonic waves, that bounces off a surface, e.g., the wedge surface 25, and creates echoes. The transducer also receives the echoes and sends them to, e.g., the controller 200, which may use the information to create an image representative of the wedge surface 25 for inspection. In one embodiment, the wedge surface inspection means 452 may be an ultrasound probe 452 configured to inspect the wedge surface 25 and to detect one or more flaws in the radii of the wedge 24, via a volumetric inspection, and to transmit image data corresponding to the volumetric inspection or surface inspection to the controller 200, e.g., via the electrical cables 110. In one embodiment, the ultrasound probe 452 may be a conventional or phase array type probe.

In yet a further embodiment, the transducer assembly 450 may further include an applicator 460 (FIG. 6) operable connected to at least one of the assemblies of the carriage 300, e.g., the frame 302, jack assembly 410 or transducer assembly 450, for supplying a couplant (not shown) to one of the wedge surface 25, the ultrasound probe 452, or both, during the inspection operation. In an exemplary embodiment, the applicator may be adjacent to the transducer probe 452 such that the couplant may be applied between the transducer probe 452 and the wedge surface 25. The applicator may apply the couplant via one or more tubes (not shown) selectively attached to a couplant container or similar housing. In yet a further embodiment, a motor, pump, or similar device may be operatively connected to the applicator for moving the couplant from its storage medium to the inspection area of the wedge surface 25. In the exemplary embodiment illustrated in FIG. 7, the applicator 460 may be integrated into the transducer assembly 450. In this embodiment, e.g., the transducer assembly 450 may include one or more slots 464, 466 operatively connected to the couplant container for applying the couplant once the transducer probe 452 contacts the wedge surface 25. The slots 464, 466 may be disposed on opposite sides of the transducer probe 452, e.g., as a forward slot 464 and a rearward slot 466.

Figure 7:
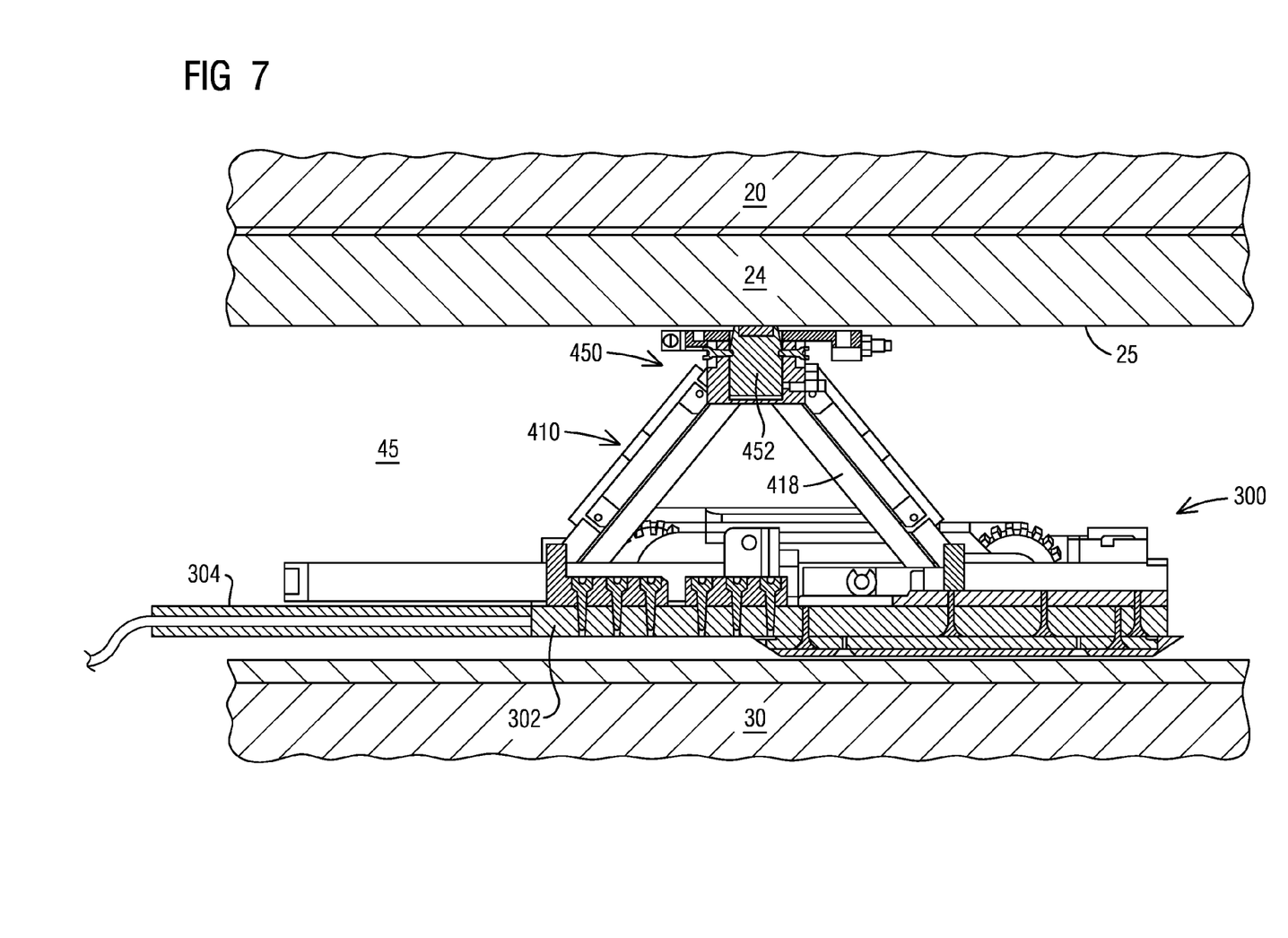
FIG. 7 is a side view of the elevated remote controlled inspection vehicle of FIG. 5, in accordance with the disclosure provided herein.

With continued reference to FIG. 6 and now FIG. 7, an embodiment of the carriage 300 is shown in an expanded position, i.e., with the jack assembly 410 extended such that the transducer assembly 450 is proximate or adjacent to the wedge surface 25. In this embodiment, upon extending the jack assembly 410, via one of the pneumatic system, hydraulic system or other extending means, the transducer ultrasound probe 452 is positioned such that inspection of the wedge surface 25 may be conducted. Additionally, upon elevating the transducer assembly for inspection, the couplant may be applied, via the applicator, to facilitate capturing data corresponding to the wedge surface 25. In another exemplary embodiment, the carriage 300 may include an eddy current probe for detecting surface discontinuities. The eddy current probe may be include in the transducer assembly 450, or selectively attached to another assembly of the carriage 300 or the frame 302.

Figure 8:
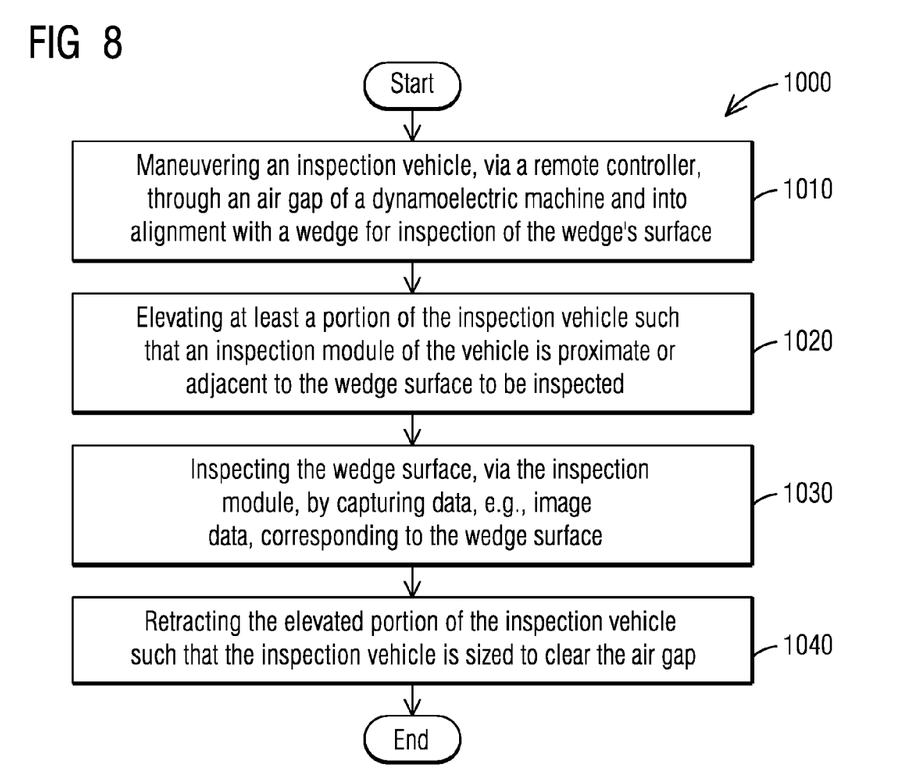
FIG. 8 is a flowchart for an embodiment of a method for in-situ inspection of generator slot rotor wedges, via an embodiment of the remote controlled inspection vehicle, in accordance with the disclosure provided herein.

With continued reference to figures and now FIG. 8, a flowchart for an embodiment of a method 1000 for inspecting generator slot rotor wedges 24 in-situ, via an embodiment of the remote controlled carriage 300 is provided.

The wedge surface 25 inspection process may proceed as follows: The carriage 300 may be maneuvered or driven, via the controller 300, through the air gap 40 of the generator 10 and into an inspection passage 50 for aligning with the wedge 24 (1010). In this step, the camera, video camera or other visual aid may be used by the operator to view the forward (or backward) progress of the inspection vehicle 300 through into the passage 50 for inspecting the wedge surface 25.

Once the carriage 300, or more particularly, the transducer assembly 450 is aligned with the wedge 24, at least a portion of the carriage 300, e.g., the jack assembly 410, is elevated or extended to about 4 inches, via the controller 200, towards the wedge surface 25 to be inspected such that the transducer probe 452 may be proximate or adjacent to the wedge surface 25 (1020). It should be appreciated that the jack assembly extension may be greater or less that 4 inches, and depending on distance between the retracted carriage 300 and wedge surface 25. The jack assembly 410 may be partially or fully extended such that the height of the carriage 300 with extended jack assembly 410 exceeds the clearance distance between the stator 30 and rotor 20 defining the air gap 40. The video camera or visual aid may also be used, e.g., by the operator/inspector, in this step, or any of the other steps to view the positioning of the carriage 300 and the elevation of the transducer assembly 450 so that an undesirable impact between portions of the carriage 300 and the wedge 24 does not occur. That is, so that no damage to the wedge 24 or component s of the carriage 300 or generator 10 occurs as a result of extending the jack assembly 410.

With the jack assembly 410 in at least the partially extended position, the method includes the step of inspecting the wedge surface 25, via the transducer probe 452, such that image data corresponding to the wedge surface 25 and the volumetric inspection may be captured and transmitted to the controller 200, e.g., via the electrical cables 110 (1030). It should be appreciated that once the transducer probe 452 is proximate to the wedge surface 25, e.g., makes contact with the wedge surface 25, one or more sound waves from the transducer probe 452 may be refracted inside the wedge 24 to detect flaws in the radii of the wedge 24.

Once the wedge surface 25 has been inspected, the operator may then maneuver or position the carriage 300, via the controller 200, to an adjacent wedge 24 or other wedge 24 for surface inspection. It should be appreciated that it may not be necessary to partially or fully retract the jack assembly 410 when positioning the carriage 300 from wedge 24 to wedge 24 for inspection. However, depending on the space available for maneuvering the carriage 300 in the passage 50, it may be preferred to at least partially retract the jack assembly 410. Upon completion of the inspection, the jack assembly 410 may be retracted, via the controller 200, such that the carriage 300 returns to a retracted position, which may allow for the carriage 300 to exit the passage 50 via the air gap 40 (1040).

In yet a further embodiment, the retraction and extension of the jack assembly 410 may correspond to the activation of the transducer assembly 450 for inspecting the wedge surface 25. That is, upon activating the transducer assembly 450 for inspection, the jack assembly 410 may begin to extend towards the wedge surface 25 for inspection. The height of extension for the jack assembly may be preprogrammed or set by the controller in this embodiment, or the height may be fixed such that a final extension of the jack assembly towards the wedge surface 25 is directed by the operator, via the controller 200. In this embodiment, a programming logic with executable instructions may be stored in a memory of a microcontroller operatively connected to the jack assembly 410, transducer assembly 450, and controller 200. The instructions, when executed by a processing circuit of the microcontroller, may cause the jack assembly 410 to extend towards the wedge surface 25 upon activation of the transducer assembly 450, via the controller 200. In this embodiment, the instructions may include instruction to monitor the operability of the transducer assembly 450 or its parts, e.g., the ultrasound probe 452 or applicator. The programming logic may further include instructions for operating, e.g., starting or stopping, the pneumatic system 420 in response to command signals from the controller 200 for operating the transducer assembly 450. In this embodiment, upon completion of the wedge surface 25 inspection or upon deactivating the transducer assembly 450, via the controller 200, the jack assembly 410, via the programming logic, may begin retracting. When the jack assembly begins to retract, the jack assembly may return to a fully retracted position, i.e., a position where the jack assembly can no longer retract, or a position that allows for the carriage 300 to clear the air gap 40. The retraction may also be a partial retraction, which may require the operator to further retract the jack assembly, via the controller, such that the carriage can clear the air gap upon exiting the generator 10.

By using the above method with the remote controlled carriage 300, the need for removing the rotor to inspect the wedge surface 25 is eliminated. Thereby, greatly reducing the down time of the generator 10.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof.

It should be noted that the terms "comprising", "including", and "having", are open-ended and does not exclude other elements or steps and the use of articles "a" or "an" does not exclude a plurality. Additionally, the steps of various methods disclosed herein are not required to be performed in the particular order recited, unless otherwise expressly stated.

We claim:

1. A generator inspection vehicle sized and configured to fit within an air gap between a stator and a rotor of the generator, the vehicle comprising:
   a frame;
   a drive module attached to the frame for maneuvering the inspection vehicle on an interior surface of the generator; and
   an inspection module operatively attached to the frame and operable to extend and retract in response to one or more signals from a remote device, and to inspect a rotor wedge surface in-situ when extended,
   wherein the inspection module comprises:
      a jack assembly configured to extend and retract in response to the one or more signals;
      a transducer assembly configured to inspect the wedge surface in response to one or more signals, and to transmit image data corresponding to the inspected wedge surface,
      wherein the transducer assembly is attached to the jack assembly,
      wherein the jack assembly is configured to elevate the transducer assembly towards the wedge surface for inspection,
      wherein the jack assembly comprises a lower portion attached to the frame,
      wherein the jack assembly comprises an upper portion attached to the transducer assembly,
      wherein the upper portion comprises a platform on which the transducer assembly is located, and
      wherein the platform is fully supported on all four corners to vertically raise the transducer assembly perpendicular the inspected wedge surface.

2. The vehicle of claim 1, wherein the drive module comprises:
   a drive train that utilizes magnetic adhesion to traverse the interior surface of the generator; and
   a motor operatively connected to the drive module and configured to provide a motive force to the drive train in response to one or more signals from a remote device.

3. The vehicle of claim 1, wherein the jack assembly includes a pneumatic system operably to elevate the upper portion of the jack assembly towards the wedge surface.

4. The vehicle of claim 1, wherein the transducer assembly comprises:
   an ultrasonic transducer and an applicator,
   wherein the ultrasonic transducer is configured to inspect the wedge surface and transmit the image data; and
   wherein the applicator is configured to apply a couplant to one of the wedge surface and the ultrasonic transducer during inspection of the wedge surface.

5. The vehicle of claim 4, wherein the couplant is applied to both the wedge surface and the ultrasonic transducer.

6. The vehicle of claim 1 further comprising:
   a visual aid operatively coupled to one of the jack assembly, transducer assembly and frame, and operable to observe and transmit information corresponding to the vehicle position relative to the wedge surface to be inspected.

7. The vehicle of claim 6, wherein the visual aid is a camera or video camera.

8. The vehicle of claim 1 further comprising:
a camera operatively connected to the inspection module and configured to transmit information corresponding to the position of the inspection module related to the wedge surface to be inspected.

9. A system for inspecting generator rotor slot wedges in-situ comprising:
a controller operatively connected to an inspection vehicle;
wherein the controller is configured to maneuver the inspection vehicle within the generator and to receive image data from the inspection vehicle during the in-situ inspection; and
wherein the inspection vehicle is sized and configured to fit through an air gap between a stator and a rotor of the generator and within a passage, and is operably configured to elevate a transducer assembly carried by the inspection vehicle to a rotor wedge surface for inspection and in response to one or more signals from the controller,
wherein the inspection vehicle comprises an inspection module comprising a jack assembly and a transducer assembly attached to the jack assembly,
wherein the jack assembly is configured to elevate the transducer assembly towards the wedge surface for inspection,
wherein the jack assembly comprises a lower portion attached to the frame,
wherein the jack assembly comprises an upper portion attached to the transducer assembly,
wherein the upper portion comprises a platform on which the transducer assembly is located, and
wherein the platform is fully supported on all four corners to vertically raise the transducer assembly perpendicular the inspected wedge surface.

10. The system of claim 9, wherein the connection between the controller and the inspection vehicle is via one or more electrical cables, and the one or more signals travel via the electrical cables.

11. The system of claim 9, wherein the connection between the controller and the inspection vehicle is wireless.

12. The system of claim 9, wherein the inspection vehicle comprises:
a drive module attached to a frame; and
wherein the drive module maneuvers the inspection vehicle within the generator in response to the one or more signals, and
wherein the inspection module elevates and inspects the wedge surface in response to the one or more signals.

13. The system of claim 12 further comprising:
a second drive module attached to the frame and disposed on an opposite side of the inspection module from the first drive module.

14. The system of claim 9,
wherein the transducer assembly is configured to inspect the wedge surface and transmit image data corresponding to the inspected wedge surface to the controller.

15. The system of claim 9 wherein the inspection module further comprises:
a hydraulic or pneumatic cylinder and piston connected to the jack assembly for elevating the transducer assembly to the wedge surface.

16. The system of claim 9 further comprising:
a camera assembly operatively connected to the inspection vehicle, and configured to transmit views corresponding to the position of the inspection vehicle within the generator to a display of the controller.

17. A method for inspecting generator rotor slot wedges in-situ, comprising the steps of:
maneuvering an inspection vehicle, via a remote controller, through an air gap of the generator and into alignment with a rotor slot wedge for inspection;
elevating at least a portion of the inspection vehicle to a surface of the wedge such that the portion of the inspection vehicle is proximate or adjacent to the surface; and
inspecting the surface, via a transducer of the inspection vehicle, by capturing image data corresponding to the surface and transmitting the image data to the remote controller,
wherein the inspection vehicle comprises a jack assembly for attaching the transducer,
wherein the jack assembly is configured to elevate the transducer towards the wedge surface for inspection,
wherein the jack assembly comprises a lower portion attached to the frame,
wherein the jack assembly comprises an upper portion attached to the transducer assembly,
wherein the upper portion comprises a platform on which the transducer assembly is located, and
wherein the platform is fully supported on all four corners to vertically raise the transducer assembly perpendicular the inspected wedge surface.

18. The method of claim 17 further comprising the step of:
upon completion of the first wedge surface inspection in-situ, maneuvering the inspection vehicle into alignment with a second wedge for inspection.

19. The method of claim 17, further comprising the step of:
retracting the elevated portion of the inspection vehicle upon completion of the surface inspection in-situ, such that the inspection vehicle is sized to clear the air gap.

* * * * *